United States Patent [19]

Jefferies et al.

[11] Patent Number: 5,078,754
[45] Date of Patent: Jan. 7, 1992

[54] FINISHING/POLISHING SYSTEM

[75] Inventors: Steven R. Jefferies; Roy L. Smith, both of Milford; Russell D. Green, Millsboro, all of Del.

[73] Assignee: Dentsply Research & Development Corp., Milford, Del.

[21] Appl. No.: 226,582

[22] Filed: Aug. 1, 1988

[51] Int. Cl.$^5$ ............................................. C09K 3/14
[52] U.S. Cl. ...................................... 51/298; 51/308; 51/309; 106/3; 106/35; 524/401; 528/49
[58] Field of Search ................. 51/298, 308, 309; 106/3, 6, 85; 528/49; 252/500, 518; 524/401; 433/125, 166

[56] References Cited

U.S. PATENT DOCUMENTS

| | | | |
|---|---|---|---|
| 991,884 | 5/1911 | Osgood | 279/103 |
| 1,043,098 | 11/1912 | Gross | 279/103 |
| 1,833,842 | 12/1928 | Leonard | 401/265 |
| 2,122,920 | 7/1938 | Russell | 32/58 |
| 2,474,684 | 6/1949 | McCaughley | 15/172 |
| 2,562,587 | 7/1951 | Swearingen | 51/309 |
| 2,735,116 | 4/1953 | Mueller | 10/140 |
| 2,929,143 | 3/1960 | Roubian | 32/1 |
| 3,267,623 | 8/1966 | Block | 51/406 |
| 3,309,772 | 3/1967 | Lieb et al. | 433/166 |
| 3,599,333 | 8/1971 | Muhler | 32/59 |
| 3,789,462 | 2/1974 | Reich | 32/59 |
| 3,964,166 | 6/1976 | Stahlman | 32/59 |
| 3,999,869 | 12/1976 | Clark et al. | 403/4 |
| 4,048,765 | 9/1977 | Samuelson | 51/293 |
| 4,055,897 | 11/1977 | Brix | 51/328 |
| 4,338,748 | 7/1982 | Elbel | 51/206 R |
| 4,447,208 | 5/1984 | Kawai | 433/166 |
| 4,512,692 | 4/1985 | Nielsen | 408/226 |
| 4,525,256 | 6/1985 | Martin | 204/159.18 |
| 4,830,615 | 5/1989 | Feinman et al. | 433/166 |

FOREIGN PATENT DOCUMENTS

| | | |
|---|---|---|
| 219684 | 6/1922 | Canada. |
| 277318 | 1/1928 | Canada. |
| 317791 | 4/1931 | Canada. |
| 340162 | 8/1934 | Canada. |
| 0369329 | 10/1937 | Canada. |
| 369329 | 10/1937 | Canada. |
| 0396664 | 5/1941 | Canada. |
| 0568235 | 12/1958 | Canada. |
| 1025672 | 2/1978 | Canada. |
| 1097957 | 3/1981 | Canada. |
| 1129216 | 8/1982 | Canada. |
| 0044701 | 1/1982 | European Pat. Off.. |
| 8708062 | 10/1987 | Fed. Rep. of Germany. |
| 8801781 | 4/1988 | Fed. Rep. of Germany. |
| 1069783 | 2/1954 | France. |

OTHER PUBLICATIONS

Tech Sheet "Scotfoam" Versatile Engineering Problem Solvers (3 pages).

*Primary Examiner*—William R. Dixon, Jr.
*Assistant Examiner*—Willie J. Thompson
*Attorney, Agent, or Firm*—Edward J. Hanson, Jr.

[57] ABSTRACT

The invention relates to a system and apparatus and a method for finishing and polishing a dental composite restorative material in a tooth. The system of the invention uses an elastomeric polymer disc which is impregnated with an abrasive for reducing of the composite, and a felt, suede, or elastomeric polymer foam element for polishing the composite. A method of using the above apparatus in a finishing/polishing system is also provided.

9 Claims, 3 Drawing Sheets

FINISHING/POLISHING SYSTEM

BACKGROUND

The present invention relates to a finishing/polishing apparatus comprising an abrasive implement for gross reduction and shaping, and a felt, suede, foam or other type polishing element for polishing. A method of using the apparatus is also provided.

Dental restoratives exhibit physical and chemical characteristics which make them suitable for use in filling, repairing or replacing teeth. Restorative materials should possess properties that closely match natural teeth with respect to structural properties such as cohesive strength, coefficient of thermal expansion and wearability. Also, aesthetic considerations such as color stability, refractive index, plaque repellency, polishability and opacity are important factors in determining whether a material is suitable for use as a dental restorative. Numerous organic compositions are used in various mixtures and proportions for use as dental composites or restoratives. These compositions usually include some type of resin, which may either be preblended or mixed by the practitioner in the office, together with other materials such as pigments, catalysts, handling agents and opacifiers. For restorative use, it is generally necessary to employ materials which are "filled", that is, to which have been added amounts of inorganic, or in some cases, organic particulate material.

Dental composite and restorative materials have good forming characteristics so that they can be shaped to fit a cavity area or molded into place in order to repair chipped or damaged teeth. Furthermore, such restorative compositions must preferably be filled with inorganic materials in order to achieve satisfactory hardness and durability during service.

The finishing and polishing of the composite is an important part of providing an aesthetically pleasing restorative.

Most prior art polishing discs used for finishing composite materials have a metal fastener in the center which is used for attaching the disc to a shaft adapted to be used in a hand held polisher. If the practitioner is not careful, the metal fastener could come in contact with and mar the composite material.

Prior art discs which are now used for shaping composites have a tendency to preferentially wear away the composite material and pluck the more rigid filler particles from the composite surface during the polishing procedure. Some such prior art discs are so abrasive that they tend to flatten natural contours of the tooth and even remove natural tooth structure when finishing or polishing the restorative material.

Therefore, the present art method for working restorative composites involves tedious working steps that use three or four grades of abrasive discs, rubber wheels and finally one or two different polishing pastes.

It is the object of the present invention to overcome the difficulties of the prior art apparatus and methods.

SUMMARY OF THE INVENTION

The present invention relates to an abrasive implement used for gross reduction, shaping and preliminary finishing of a composite restorative. The abrasive implement of the invention comprises an elastomeric polymer reinforced with an abrasive powder. The prepolymer used to make the elastomeric polymer of the disc may be light cured, thermally cured or chemically cured or a combination thereof. The abrasive powder comprises about 5-95% by weight of the composition and preferably will be about 25-90% and most preferably about 35-80% by weight of the composition.

The invention also relates to a polishing element for polishing dental features comprising an element of napped material selected from the group comprising natural fibers, synthetic fibers, synthetic foam, natural or synthetic sponge and similar material and a mixture thereof. Preferably the polishing element will be made from felt, suede or a foamed plastic. The nap of the material used to make the polishing element will be capable of carrying a lapping material when said element is rotated.

In an alternative embodiment of the polishing element, the polishing element will be made of an elastomeric polymer of the kind used to make a finishing implement and will have fine abrasive particles embedded therein.

The invention also relates to a composite finishing/polishing system comprising the abrasive implement of the invention for reducing or finishing the composite; and a polishing element of the invention for polishing the composite, formed from an elastomeric polymer, or a natural or synthetic fiber material, having a nap capable of holding and carrying a lapping paste under rotation.

The invention also relates to a method of finishing and polishing a restorative composite comprising the steps of shaping the composite using the abrasive implement of the invention, and then polishing the composite using the polishing element of the invention.

Using the apparatus and method of the invention, a simplified finishing procedure involving fewer steps leading to a superior composite restorative surface has been demonstrated. A final polish utilizing a felt cup or a polyurethane cup in combination with sequentially a 15 micron and a one-micron abrasive was demonstrated to yield not only a superior surface in terms of smoothness and luster, but has been shown to be a very effective system in simultaneously polishing resin and filler particles. In an alternative embodiment, the use of certain synthetic polymers make possible finishing with a dry element only and polishing with a one-micron abrasive paste.

DESCRIPTION OF THE ILLUSTRATED EMBODIMENT

The finishing/polishing system of the present invention desirably comprises the use of two parts.

First, an elastomeric shaping and preliminary finishing implement which is impregnated with an abrasive is provided for shaping and reduction. This implement may contain 80-175 micron abrasive powder and desirably contains approximately 90-150 micron abrasive powder and preferably contains approximately 100-120 micron abrasive powder. A second part of the system used is a polishing element.

It is believed that the two part finishing/polishing system of the invention will be sufficient for preparing most composite fillings. In the case of extreme overcontouring of composite material, however, it may be desirable to first prepare the composite by gross reduction using a fluted bur, a diamond bur, or an abrasive disc loaded with coarse abrasive particles.

The preferred abrasive powder used in the invention is aluminum oxide, preferably x alumina. Those skilled in the art will recognize that other similar abrasives have been characterized and will be similarly useful in the invention. To be effective, the particles of the abrasive powder should have a hardness at least equal to the hardness of the filler particles of the composite, and preferably will have a greater hardness. In the preferred embodiment the abrasive used will have a hardness of between about 5.5 and 10, preferably about 7-10, and most preferably about 8-9 on the mohs scale of hardness. Exemplary of such abrasives are carborundum, topaz, quartz, and diamond dust.

The abrasive implement and the polishing element of the invention may be in the form of a cup, pad, disc, cone, cylinder or any other shape that may be suitable for use as a finishing implement or a polishing element.

A polishing element may be made by carving the element from a solid sheet of napped material selected from the group comprising natural fibers, synthetic fibers, synthetic foam, natural or synthetic sponge and a mixture thereof. Those skilled in the art will also recognize that other similar materials may also be used to make the polishing element of the invention. Those skilled in the art will recognize that other means, such as molding, casting, and grinding, may be used for making the polishing element of the invention. In the illustrated embodiment, the polishing element may be felt, suede, an elastomer such as polyurethane foam or a soft formed plastic.

The felt or suede materials may be natural or may be formed from synthetic materials having a consistency and density such that they resemble natural felt or suede. Such materials made of polyurethane, and a polyurethane foam, are available from Scotfoam Corp., 1500 East Second Street, Eddystone, Pa. 19013. A preferred polyurethane felted foam material for use in the invention is a firmness 10 non-reticulated felted foam made from 90 ppi (pores per linear inch) base stock as defined by Scotfoam Corp. The synthetic suede is a firmness 12 reticulated felted foam with a compression ratio of 12:1.

Figure 1:
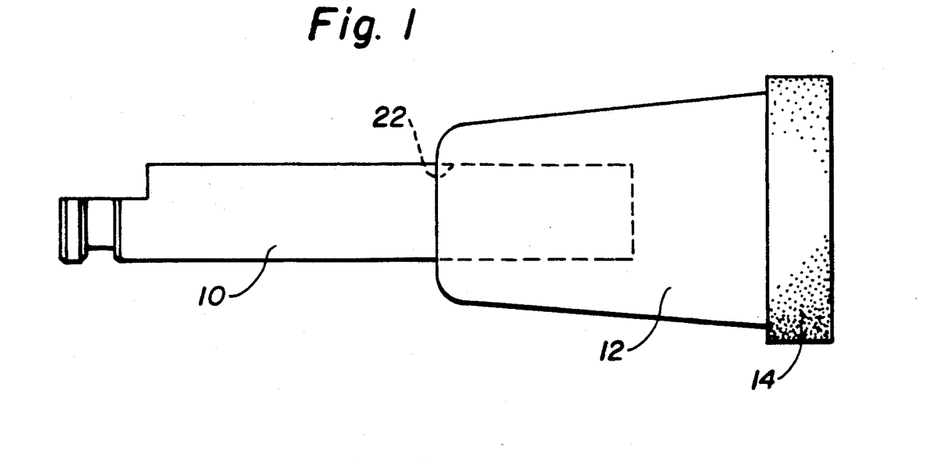
FIG. 1 illustrates the apparatus of the invention having a rigid shank, an intermediate segment made of elastomeric material, and a polishing element.

With reference now to FIG. 1, a finishing implement comprising a disc 14 of the invention may be mounted on elastomeric material 12 which is mounted on a rigid shank 10 which is adapted to fit into the chuck of a standard polishing tool. In the illustrated embodiment, elastomeric material 12 has a hole 22 therein which is adapted to receive rigid shank 10 which may be adhesively or mechanically attached to elastomeric material 12. In the preferred embodiment, the elastomeric material is molded onto the rigid shank. Other means of attaching rigid shank 10 to elastomeric material 12 will be apparent to those skilled in the art. A finishing disc 14 may be attached to the elastomeric material 12 by means known to those skilled in the art, for example, by using a pressure sensitive adhesive coated on elastomeric material 12 or finishing disc 14 or both.

Rigid shank 10 may be made of metal, stiff plastic, cardboard or any other material having strength suitable for supporting an abrasive disc or polishing element in a polishing tool.

The use of elastomeric material 12 as an intermediate member between rigid shank 10 and finishing disc 14 reduces the shock of the impact of finishing disc 14 on the tooth thereby providing a more mild finishing and polishing action.

Figure 3:
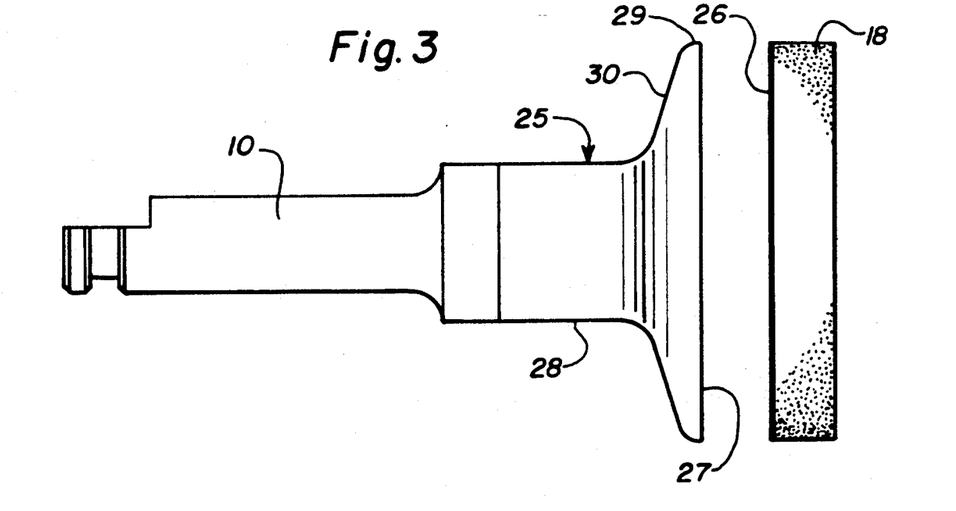
FIG. 3 illustrates an exploded view of a polishing element attached to a finishing implement.

With reference now to FIG. 3, in an alternative embodiment of the finishing disc of the invention a finishing disc 25, which is made of a rigid, resilient elastic polyurethane, comprises a circular working surface 27, joinder area 28 having a substantially smaller diameter than said working surface 27 by which the finishing disc 25 is attached to a mandrel, a back surface 30 providing a transition between the working surface 27 and the joinder area 28, and working edge 29 formed where working surface 27 and back surface 30 meet. Working edge 29 may be used to finish composite material on hard to reach areas, such as between the restorative material and an adjacent tooth.

As used herein, rigid represents that the polymeric material of the finishing disc of FIG. 3 is stiff so that it maintains its general shape even when engaged in finishing a restorative. By resilient it is meant that even though the disc maintains its general shape, there is sufficient give in the polymer of the disc so that the working surface 27 of the disc may bend to conform the shape of the disc to the shape of the tooth. By elastic or elastomeric it is meant that after the disc is bent, it will return substantially to its original shape when pressure on the disc is removed.

Figure 11:
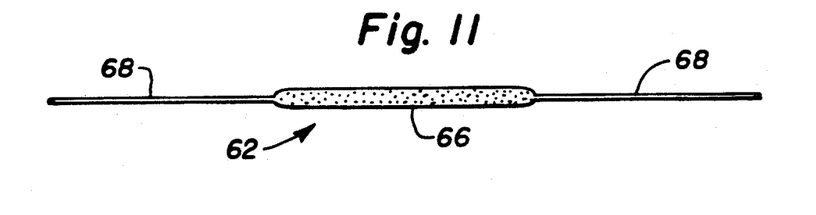
FIG. 11 illustrates a precision lapping film strip used for interproximal finish.
Figure 12:
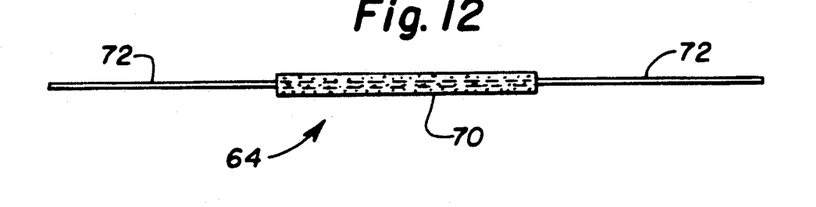
FIG. 12 illustrates an additional embodiment of a precision lapping strip.

In addition to working edge 29 of finishing disc 25, in a complete finishing/polishing system, there is provided precision lapping films (strips) as illustrated in. FIGS. 11 and 12 for finishing and polishing the interproximal areas of the teeth.

Finishing disc 25 may be of a size convenient for the finishing action required. In the illustrated embodiment, the diameter of working surface 27 will be about ⅜ to about 11/16 inch and preferably will be about 9/16 inch. The finishing disc 25 may have any length convenient for use on mandrel 10 and in the illustrated embodiment will be about 0.20 to about 0.24 inch. The diameter of joinder area 28 approximates the diameter of mandrel 10.

Since the composition of finishing disc 25 includes an abrasive powder, back surface 30 of the disc may be used for a finishing action where applicable.

Although the abrasive filled polymer used to make the abrasive disc is rigid, the abrasive disc is also resilient. Because of this property, and because of the results achieved, it is believed that the resiliency of the finishing disc causes the finishing disc to bounce away when a non-yielding filler particle is encountered in the restorative and thereby substantially prevents snagging. Similarly, it is believed that abrasive particles yield into the body of the finishing disc and/or are lost from the finishing disc in preference to gouging or scratching the restorative since forces needed to scratch the restorative are apparently greater than those needed to move the abrasive particles in the polymer of the finishing disc. Similarly, it is believed that the finishing disc conforms somewhat to the shape of the tooth causing the finishing action to be distributed over a relatively large area which enables a broad smooth surface to be achieved.

The same type of action can be described for the softer, more resilient polishing elements used in the finishing/polishing system of the invention.

Since the polymer used to make a finishing disc is filled with abrasive particles, it can be said that the polymer is reinforced with the abrasive and that the abrasive is embedded within the polymer as an integral part thereof.

Because of the rigidity of finishing disc 25, finishing disc 25 may be adapted for mechanical attachment to mandrel 10. Means of mechanical attachment will be apparent to those skilled in the art and alternatively, finishing disc 25 may be molded onto mandrel 10 or fixed to mandrel 10 by use of an adhesive.

Referring to FIG. 1, in one embodiment of the present invention, when the finishing procedure is complete, the finishing disc 14 may be removed from elastomeric material 12 and be replaced with a polishing element in the form of a disc. Alternatively, after its use, the finishing disc 14 may be retained on the elastomeric material 12, and the polishing disc may be attached directly to the finishing disc 14 by using, for example, a pressure sensitive adhesive.

Figure 2:
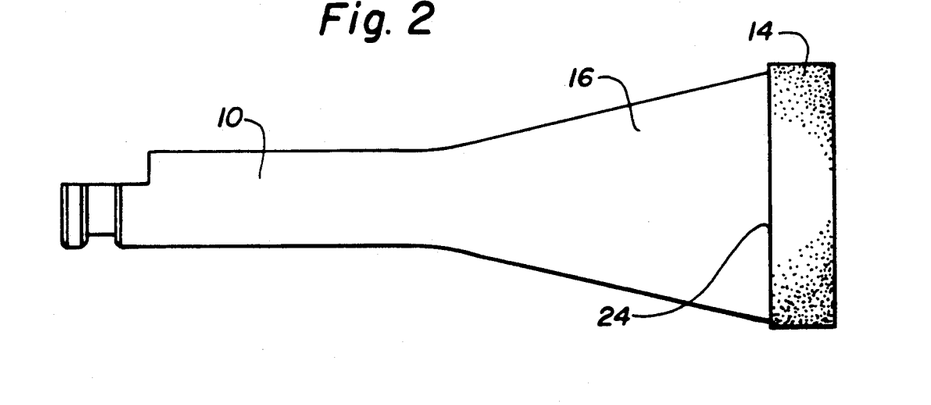
FIG. 2 illustrates an alternative embodiment of the invention having a polishing element connected directly to a rigid shank.

In an alternative embodiment of the invention, as illustrated in FIG. 2, the shank 10 may have a cone shaped taper 16 which terminates in land 24 which is adapted to receive a finishing disc 14 or a polishing disc directly thereon.

In another embodiment, as illustrated in FIG. 3, a finishing disc 25 may be molded onto a shank 10. After the practitioner is finished using finishing disc 25, a polishing element 18 in the form of a disc is attached to finishing disc 25 by means of pressure sensitive adhesive 26. Those skilled in the art will recognize that pressure sensitive adhesive 26 may be applied to polishing element 18 at the factory and the adhesive may be protected until it is used by a releasable paper covering.

Figure 4:
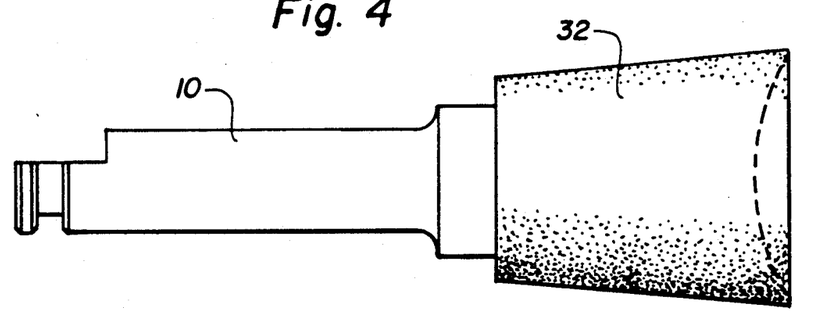
FIG. 4 illustrates a polishing element of the invention.
Figure 5:
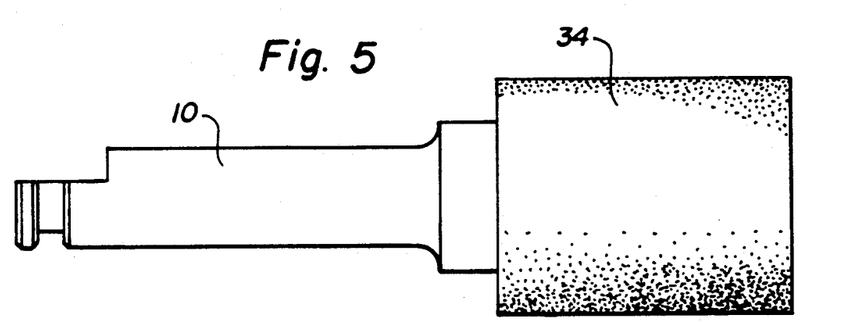
FIG. 5 illustrates an alternative polishing element of the invention.

As illustrated in FIGS. 4 and 5, the polishing elements 32 and 34 may be molded to shank 10 and may be in the form of a polishing cup having a tapered cylindrical or cylindrical shape. Other shapes for a polishing element will be apparent to those skilled in the art.

Figure 6:
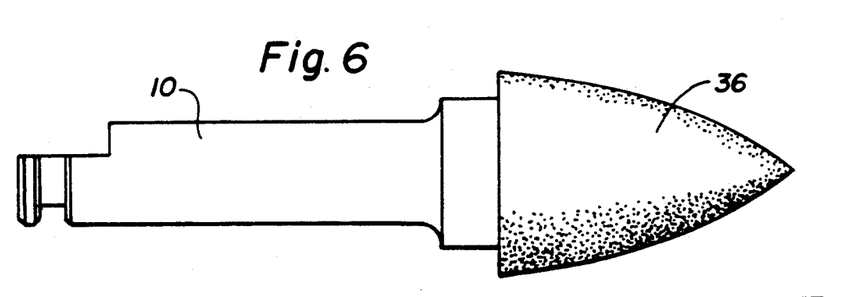
FIG. 6 illustrates an abrasive implement in the shape of a cone.

Similarly, as illustrated in FIG. 6 the abrasive implement 36 may be in the shape of a cone. Other suitable shapes for the abrasive implement will be apparent to those skilled in the art.

Figure 7:
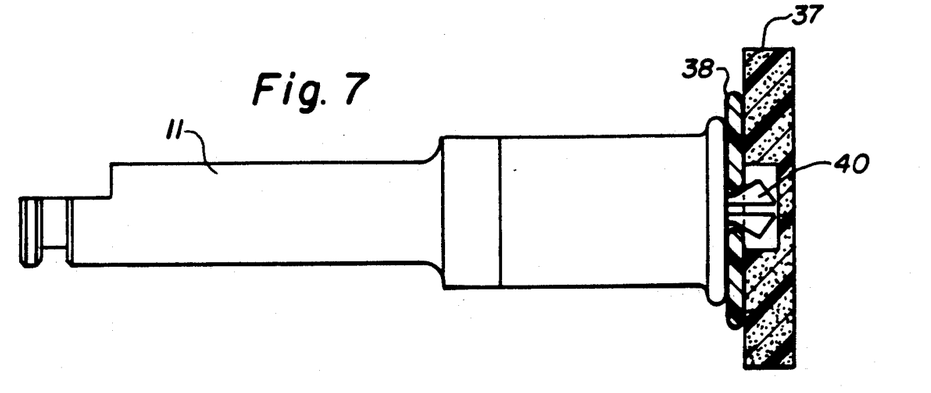
FIG. 7 illustrates a polishing element disc attached to a conventional mandrel.

As illustrated in FIG. 7 a finishing or polishing element 37 may be made with a snap on ring 38 integrally connected therewith which can be used to attach the polishing element to a conventional mandrel 11 which has a snap attachment 40 used to hold prior art finishing implements and polishing elements.

In an alternative embodiment, a polishing element can be made of an elastomeric polymer of the same type used to make the finishing implement and in the same manner but will have smaller abrasive particles embedded therein.

Figures 8, 9, 10:
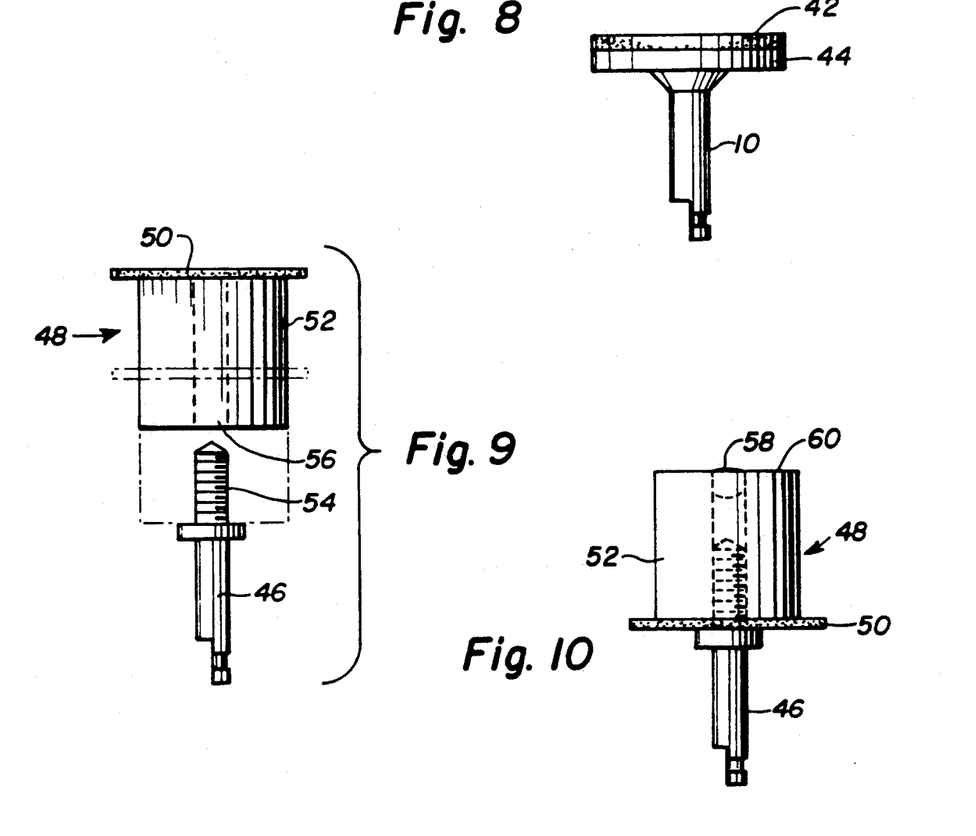
FIG. 8 illustrates an embodiment which contains both a finishing implement disc and a polishing element.
FIG. 9 illustrates an embodiment which has a reversible finishing/polishing device attachable to a shank.
FIG. 10 illustrates the embodiment of FIG. 9 in which the finishing/polishing device has been reversed.

With reference now to FIG. 8, in a further embodiment of the invention, a finishing implement 42 and a polishing element 44 are mounted together on the same shank 10. In such an embodiment finishing implement 42, comprising a circular pad or disc of, for example, polyurethane polymer imgregnated with aluminous oxide, provides the outermost portion of the device. In its operation the practitioner uses the finishing implement 42 for finishing a restorative until finishing implement 42 substantially wears away, and continues to use the device for polishing the restorative using the underlying polyester film or foam polishing element 44. Alternatively, if only light finishing is required, the practitioner may remove finishing implement 42 from the device to continue with the polishing procedure.

With reference now to FIGS. 9 and 10, in a further embodiment, the device may comprise a reversible portion 48 that comprises finishing implement 50 in the form of a disc, 10 mm in diameter and about 0.4-0.6 mm thick, which comprises an elastomeric polyurethane polymer containing aluminous oxide abrasive, and polishing element 52 which comprises a polyurethane foam cylinder about 5-9 mm in diameter and about 3-6 mm long. The cylinder 52 and the disc 50 have a threaded guide hole 56 therein adapted to receive threaded end 54 of shank 46.

In the illustrated embodiment, it has been found that using a shank 46 made of metal, for example stainless steel, provides a device with particularly beneficial properties.

Those skilled in the art will recognize that besides providing threads on shank 46, other suitable means may be provided for retaining reversible portion 48 on shank 46.

In its use, reversible portion 48 may be first used with finishing disc 50 distal from shank 46, (as illustrated in FIG. 9) for finishing a restorative material, and reversible portion 48 may be removed from shank 46 and replaced on shank 46 with disc 50 proximal to shank 46 (as illustrated in FIG. 10) to proceed with a polishing step. In addition, a polishing paste 58, such as PRISMA ®-GLOSS ™ may be applied to the working surface 60 of cylinder 52 to facilitate the polishing.

With reference now to FIGS. 11 and 12, as part of a total finishing polishing system, it is desirable to include a precision lapping strip 62 and/or 64 to provide for interproximal finishing. It will be recognized by those skilled in the art that such lapping strips may be used for finishing/polishing of any kind.

In the illustrated embodiment, precision lapping film 62 comprises abrasive area 66 which preferably is made of a tough but thin strip of plastic, such as Mylar, which is impregnated with aluminous oxide abrasive particles. Abrasive area 66 is attached to polymeric film handles 68, e.g. polyester film handles, that can be used by the practitioner to control the lapping strip during the finishing/polishing procedure.

In embodiment 64, abrasive area 70 may comprise a polymeric foam (made of the same materials described for manufacture of the polishing elements described above), and handles 72 may comprise dental floss or fiber handles which also may aid in the polishing procedure.

As used herein, both the finishing and the polishing involve abrasive action. In the finishing procedure relatively larger abrasive particles are used to rapidly remove composite material making an even but relatively rough surface. In the polishing procedure, smaller abrasive particles remove the composite material less rapidly, and the polymer itself provides a buffing action to provide a very smooth surface. When a lapping paste is used with a polishing element, a very lustrous surface is obtained.

Accordingly, as illustrated herein, description relating to a finishing implement will apply to a large degree to a polishing element having a structure similar thereto, differentiated from the finishing implement by having a relatively fine abrasive embedded in the polymer thereof.

In the preferred embodiment the polymer used in making the finishing disc of the invention will be low molecular weight polyurethane similar to that disclosed in U.S. patent application Ser. No. 120,269 filed Nov. 13, 1987 having the same assignee Said Ser. No. 120,269 is incorporated herein by reference. Those skilled in the art will recognize that other polymers, such as polyesters, polyethers, polyimides, silicone and neoprene rubber may be used for making the finishing disc of the invention when they are formulated to have the desired rigidity, resilience and elasticity demonstrated by the illustrated polyurethane implements described herein.

In the preferred embodiment the prepolymer used to make the finishing implement of the invention will have a molecular weight of about 1500 to about 2500 and will have a viscosity of between about 10,000 and 35,000 cps at 25° C.

Accordingly, in the illustrated embodiment, the finishing/polishing system comprises a rigid, elastic, and resilient polyurethane abrasive finishing implement having an abrasive powder embedded therein having a mean particle size of about 0.025-300 microns. The finishing implement of the invention will be suitable for finishing a composite when the particle size of the abrasive is in the large end of this range and preferably will have embedded therein an abrasive having a mean particle size of about 80-175 microns and most preferably about 90-150 microns. The finishing implement will be more suitable for polishing when having a mean particle size in the lower end of the range and when used for polishing will preferably have a mean particle size of about 0.025-30 microns and most preferably 0.25-15 microns.

When using the finishing implement or polishing element of the invention, the practitioner needs only to wet the finishing implement or polishing element with water and commence with the finishing/polishing procedure. Lapping paste may be used with either the finishing implement or the polishing element but the use of the paste is not necessary to achieve a smooth surface because of the abrasive embedded in the finishing implement and the abrasive impregnated in the polishing element. To achieve a high luster, however, it is desirable to use a lapping paste in conjunction with the finishing implement and polishing element of the invention. The use of lapping paste appears to provide the final ingredient required for a highly lustrous surface and, apparently because of the resiliency of the finishing implement, even in the case where a finishing implement having an abrasive having a mean particle size approaching 95 is used, the abrasive in the lapping paste provides polishing action to the exclusion of the abrasive in the finishing implement, to provide a smooth, polished surface.

As used herein, impregnated indicates that abrasive is incorporated into the intertices of the natural or synthetic fibers of a polishing element as differentiated from the inclusion of the abrasive particles into the polymer used to make a finishing implement or polishing element and the embedding of abrasive particles therein.

Those skilled in the art will recognize that there may be an overlap between finishing action of the finishing disc and polishing action of the polishing element of the invention depending on the size of the abrasive particles used and how the practitioner uses them.

In the preparation of the polymer composition for making the polyurethane finishing disc, the prepolymer composition is loaded to comprise about 5-95% by weight of abrasive powder. Preferably the prepolymer composition will contain about 25-90% by weight abrasive powder, and in the preferred embodiment will contain about 35-80% by weight abrasive powder.

Alternative to the synthetic polymer polishing elements described above, the finishing/polishing system may comprise a polyurethane abrasive finishing implement and a natural felt, or suede polishing element. A lapping paste containing a one micron abrasive is preferably used with the felt or suede element for the polishing action and the fiber of the felt or suede will preferably be impregnated with an abrasive having a mean particle size of between about 0.025 and 50 microns. As will be apparent to those skilled in the art, if desired, the practitioner may use more abrasive lapping pastes with the felt or suede polishing element of the invention, up to about 15-20 microns, if a more agressive polishing action is desired. In terms of overlap between finishing and polishing, 10-50 micron abrasives may be considered to provide a fine finishing or a rough polishing action.

The polymeric urethane binder appears uniquely suited to deliver abrasive in a finishing implement. In one embodiment, the intermediate abrasive character of the implement allows for simultaneous reduction and finishing, and subsequent polishing (using a lapping paste) of composite surfaces using one implement. The implement is sufficiently flexible to allow its use on different shapes and contours. The implement material can also be fabricated in a variety of shapes and sizes to allow easy access in all areas of the mouth. An aliphatic polyurethane as described herein has been found to have properties such that it is particularly suitable for making the finishing implement.

The finishing/polishing system maintains tooth contours while reducing the restorative material in a controlled fashion. Natural contours and convexities of teeth are maintained without reduction of natural tooth enamel at the margins of the restorative. This process requires fewer steps at a net saving in time. .

The finishing/polishing system of the invention has the advantage over prior art rubber polishing systems in that the disc and polishing element of the invention does not mar the restorative surface or generate heat as do rubber polishing elements. The polishing element also acts as a shock absorber which facilitates the above described action and the polishing action.

A final polish utilizing a felt cup and one-micron aluminum oxide abrasive in a lapping paste imparts a glossy luster to composites unattainable with current finishing systems. The intersurface frictional forces between the working surface of the polishing element and lapping paste and the composite surface appear uniquely suited to polish plastic and filler particles simultaneously. The resultant effect is a highly lustrous surface.

In the preferred embodiment, the polishing element will be a felted foam elastomeric polymer element.

An abrasive implement or a polishing element made of polyurethane significantly reduces splatter of polishing or prophy paste when compared to the use of a rubber element and gives a superior finishing result. The elastomeric polymer foam polishing element maintains a more even amount of polishing paste in contact with the surface of the tooth and restorative. Finally, the element is wear resistant so that its function in a single use is not impaired, but it undergoes a sufficient amount of wear so that at the end of a single use it is unuseable for another patient. Thus, reuse of the element is undesirable, and the possibility of cross-contamination by reuse is reduced.

The typical finishing action of a prior art sandpaper disc is the wearing away of the resin matrix preferentially to the filler particles, and filler particles are eventually exposed to such an extent that they exfoliate or are plucked from the resin surface. This process limits the resultant luster attainable.

The felt element and elastomeric polymer foam element of the invention appear to function uniquely as abrasive carriers to provide the proper combination of aggressive action required to polish the more rigid filler particles and a milder buffing response effective on the resin portion of the composite.

The combination, therefore, of an abrasive elastomeric polymer disc for contouring and gross reduction followed by the action of a felt, suede or foam polishing element functioning as an abrasive carrier have demonstrated superior polish/buffing action on dental restoratives when compared to existing finishing systems.

The abrasive disc(s) is formed by thermal, light, or chemical polymerization of the urethane prepolymer reinforced with an abrasive powder such as aluminum oxide.

The composition of the resin used to make the preferred embodiment of the invention is described as follows:

| Composition of Urethane Resin | |
|---|---|
| | % |
| Polypropylene glycol 2000 mol. wt. | 73.86 |
| Tin octoate catalyst | 0.05 |
| Trimethylhexamethylene diisocyanate | 15.52 |
| Hydroxyethyl methacrylate | 10.57 |
| | 100.00 |

The two terminal hydroxyl functions of polypropylene glycol are reacted with trimethylhexamethylene diisocyanate to yield an isocyanate-terminated urethane polyol. The isocyanate- terminated urethane polyol is then capped with hydroxyethyl methacrylate to form the urethane prepolymer resin. Tin octoate is the urethane catalyst. The resin viscosity is approximately 15,000 to 30,000 cps at 25° C. The resin can be thermally polymerized as well as photopolymerized.

| Resin Activation | | | |
|---|---|---|---|
| | Photo | Thermal | |
| | % | % | % |
| Resin | 98.99 | 99.00 | 99.25 |
| Camphorquinone | 0.15 | 0.00 | 0.00 |
| butylhydroxytoluene | 0.05 | 0.00 | 0.00 |
| Benzoyl Peroxide | 0.00 | 0.00 | 0.75 |
| Lauroyl Peroxide | 0.00 | 1.00 | 0.00 |
| 4-Ethyldimethylaminobenzoate | 0.81 | 0.00 | 0.00 |
| | 100.00 | 100.00 | 100.00 |

Photopolymerization of the resin is accomplished utilizing camphorquinone as visible light absorber and 4-ethyldimethylaminobenzoate as reducing agent. Thermal polymerization of the resin, however, is preferred in the molding and fabrication of the abrasive discs.

| Abrasive Dope Composition | |
|---|---|
| | % |
| Urethane Resin | 27.00 |
| Pyrogenic Silica | 3.00 |
| Aluminum Oxide | 70.00 |
| | 100.00 |

Pyrogenic silica is utilized to enhance the tear strength of the polymerized resin. The particle size of aluminum oxide ranges from about 0.025 to approximately 150 microns in diameter depending on the abrasive action required.

Disc Preparation

A metal or plastic mandrel is inserted into an appropriately formed mold cavity. The mold cavity is filled with the abrasive dope, and polymerization is accomplished at approximately 250° F. (121° C.). Preferably at least a small amount of pressure will be applied to the abrasive dope during molding. The retentive portion of the mandrel is positioned in the mold cavity so that the neck of the disc becomes securely attached to the mandrel. The abrasive character of the disc becomes a function of the particle size of the aluminum oxide.

A second component of the Composite Finishing-/Polishing System may comprise a polishing cup mounted on a mandrel. Polishing elements shown to be effective were carved from a solid piece of polyurethane felt and foam and mechanically attached to the end of a mandrel. The element functioned as carrier for the one-micron aluminum oxide lapping paste in the final buffing action. The composition of the element can be of natural or synthetic fibers or some combination thereof as well as formed plastics with sufficient nap to impart buffing action in the described procedure.

In one embodiment the polishing element, such as for example the elastomeric polymer foam polishing element, can be adhesively attached to a plastic shank which has on it an elastomeric rubber intermediate segment. In a second possible configuration a rigid plastic element, which could be part of the mandrel itself, can be attached directly to the elastomeric polymer felt finishing surface.

In another embodiment, elastomeric polymer foam discs which have a thickness of 1 to 2 millimeters, or slightly thicker, could be retained on the intermediate finishing disc surface by use of a pressure sensitive adhesive. In this embodiment the practitioner, once completing use of the intermediate finishing disc, would simply wash and dry the surface of the disc and then apply the elastomeric polymer foam polishing element directly thereon using a pressure sensitive adhesive to hold the polishing element on the intermediate disc. Finishing paste would then be placed on the tooth surface as well as on the surface of the polishing element and then applied with low speed to intermediate speed to provide final finishing and polishing.

Using a finishing disc or polishing element that is attached to the mandrel using a pressure sensitive adhesive has the additional advantage that the disc can be used with any conventional polishing apparatus that uses a mandrel that is held in the chuck of a conventional polishing apparatus.

As will be recognized by those skilled in the art, the apparatus and method of the present invention can also be adapted to be used for removing stain and the polishing of enamel and other tooth surfaces in the course of a normal dental appointment or checkup.

The use of the polishing system of the invention is illustrated by the following examples.

EXAMPLE 1

A class IV restoration was placed using a small particle, barium-glass filled composite sold under the name Prisma Fil ® by Dentsply International Inc. The restoration was large, involving the facial, proximal, incisal, and lingual surfaces. After placing the uncured restorative material in the cavity preparation, the material was shaped and contoured to the approximate shape of the restoration. The restorative material was cured with visible light concentrated in the blue region of the visible spectrum. After curing the restorative material, an intermediate finishing implement disc having a diameter of about 9/16 inch and a shape as illustrated in FIG. 3 (attached to a locking mandrel) and having a 120 micron abrasive (x alumina, from Meller Alumina) embedded therein, was placed in a low to intermediate speed handpiece (Titan-S). With the disc rotating, the surface and margins of the composite were reduced and smoothed simultaneously. As the intermediate finishing implement disc lacks any metal mandrel in the center, the entire surface of the disc can be used to finish the surface of the composite restoration. The surface becomes smooth with a dull satin luster. At the completion of this step, the surface of the composite was rinsed and dried. The top flat surface of the intermediate finishing implement was rinsed with water and dried. A polishing element comprising a flat, synthetic foam disc, as described in this disclosure, was provided with a pressure sensitive adhesive and an overlaying protective paper backing. The paper backing was peeled away from the adhesive with care not to touch the adhesive surface, and the foam polishing disc was attached to the surface of the intermediate finishing disc with moderate pressure. The operator centered the polishing foam squarely so that it covered the surface of the intermediate finishing disc symmetrically. The surface of the tooth and the restoration were covered with a 15 micron polishing paste and the foam - disc polishing element was applied to the tooth-restoration surface with rotation at low to intermediate speed. As finishing proceeded, small additions of water from a hand-held syringe were applied to the surface to aid in polishing. After about 60 seconds of polishing with a glycerin based polishing paste with a 15 micron abrasive, the tooth-restoration surface was thoroughly rinsed to remove all of the 15 micron paste. The surface was then dried. The surface of the conjugate polishing device was also rinsed to remove all remaining 15 micron paste. A 1 micron polishing paste sold under the name of PRISMA ®-GLOSS ™ was applied to the surface of the foam disc and the tooth surface. Low to moderate speed rotation was effected. As polishing proceeded, small increments of water were added to facilitate polishing. The polishing with the 1 micron paste requires from 30 to 90 seconds. The tooth-restoration surface was rinsed to remove all polishing paste and the surface was dried. The surface revealed a highly reflective surface without scratches or apparent defects, even when viewed at 7 times normal magnification.

The above technique offers the advantages of not having to change elements on the low speed handpiece, enhanced speed of procedure, and an excellent polished surface that results from the elements and technique of the procedure.

EXAMPLE 2

The method of Example 1 was followed except that the cured restoration prior to finishing possessed large amounts of excess, which required gross reduction with a 12 fluted finishing bur. After this step was accomplished, the finishing and polishing of the restoration was accomplished as described in Example 1.

EXAMPLE 3

The method of Example 1 was followed except that a polishing disc composed of a felt prepared from natural fibers with the pressure-sensitive adhesive and paper backing was used. A felt disc composed of wool was used and the felt disc was attached to the surface of the intermediate finishing element in a fashion similar to that described in Example 1.

EXAMPLE 4

The method of Example 1 was followed except that the final polishing element was attached to a separate mandrel and was engaged into the low to intermediate speed handpiece in the same fashion as the intermediate finishing disc. The polishing element resembles a cup in this instance and was composed of a synthetic foam. Example 4 was duplicated also with a synthetic felt.

EXAMPLE 5

A small particle glass, PRISMA-FIL ® restoration was placed on the entire facial surface of an extracted upper cuspid. The right half of this veneer was finished with all four sequential discs of the 3M D SoftLex ® System. The coarse, medium, and fine SoftLex ® discs were each applied to the right half of the veneer rotating in a low-speed, contra-angle handpiece (Midwest) for a contact time of 45 seconds. An extra-fine SoftLex ® disc was then applied to the right half of the veneer for approximately 45 seconds. Two more extra-fine discs were applied in identical fashion until no further improvement in surface finish was noted.

The left half of this same anterior PRISMA-FIL veneer was finished and polished in the following manner:

1. The intermediate finishing disc of the invention was applied in a rotating fashion, using a low-speed, contra-angle handpiece (Midwest) for a contact time of 45 seconds.

2. A natural fiber, felt, polishing element, as described herein was used to apply a one (1) micron, aluminum oxide polishing paste, PRISMA ®-GLOSS ™, to the left half of the veneer. The PRISMA ®-GLOSS TM was applied dry to the veneer surface for 30 seconds, a small amount of water was placed on the veneer, and an additional increment of PRISMA ®-GLOSS TM was applied for another 30 second period. The left half of the veneer was rinsed and dried.

Direct visual (unaided) and magnified examination (1× to 7×) clearly demonstrated the improved surface prepared on the left half of the veneer by the method of the invention.

EXAMPLE 6

The method of Example 5 was repeated exactly, except for the use of a 10-firmness non-reticulated felted foam (Scotfoam Corp.) polishing element. The results of this procedure were identical to that obtained in Example 5.

EXAMPLE 7

A small particle glass restoration (PRISMA-FIL ®), was placed at an anterior direct composite veneer on the facial surface of an anterior cuspid. The material, as in other examples, was cured with a visible light photopolymerization unit. After placement and light-curing, the anterior PRISMA-FIL ® veneer was contoured and finished with the intermediate finishing disc for approximately 45 seconds. The disc and attached mandrel were rotated in a low-speed, MidWest, contra-angle handpiece. After use of the intermediate finishing element, the surface of the veneer was rinsed with water and dried with an air syringe.

The intermediate finishing element was removed from the low-speed handpiece. A polishing element, consisting of a disc of 20-900-Z Scotfelt reticulated felted foam attached to a plastic mandrel (see FIG. 2), was engaged into the low-speed handpiece. The polishing element was applied to the PRISMA-FIL ® veneer while rotating in the low-speed handpiece. The polishing element in the low-speed handpiece was applied to the composite surface, dry, without paste for 30 to 90 seconds. This step provided some degree of microscopic finishing. After this step, a 1 micron, glycerine-based polishing paste (PRISMA ®-GLOSS ™) was applied to the surface of the composite veneer, initially without water, then with small increments of water to the surface of the veneer. The entire application period for the PRISMA ®-GLOSS ™ paste was approximately 30 to 90 seconds. The paste was then rinsed from the surface of the veneer. The veneer was then dried with an air syringe and a dry cotton roll. The resultant surface had a high luster without surface defects, even when viewed under 7× magnification.

A tinted adhesive may be used to allow the practitioner the ability to center the polishing element disc on the finishing disc. This tinted adhesive may form a colored border just inside the outer radius of the polishing element. The practitioner places the finishing disc directly over, and matching, edge for edge, the circular tinted adhesive area. Alternatively, colored markings may be placed under the adhesive layer on the polishing element to also aid in centering.

Another approach to aid in centering the adhesive-backed polishing element is a rigid or semi-rigid package which permits the finishing disc to contact the adhesive-backed polishing element in a fixed orientation.

EXAMPLE 8

It has been found in the gross reduction of a composite material that by using burs made of tool steel or stainless steel that significant improvement in control and finish is obtained. Burs made of tool steel and stainless steel have a Rockwell hardness of from 50 to 65, whereas carbide finishing burs, which are commonly used for gross reduction of composites, are much harder. After using steel or stainless steel finishing burs, the resultant surface can be reduced to an anatomic (contoured), but mirror-like surface with just one additional step; application of a 1 micron aluminous oxide polishing paste with a 20 or 15 grade polyurethane foam cup. This cup may be attached to a steel mandrel whose tip penetrates into the foam. See FIGS. 9 and 10. Alternately, a plastic or steel mandrel with a flat circular platform (7 mm diameter by 1.4 mm thickness) can accept a foam cup or disc which has applied on it a pressure sensitve adhesive. See FIG. 8.

EXAMPLE 9

The polyurethane foam cups and disc can be used as prophy cups for applying prophy paste after a routine cleaning appointment. If reticulated foams are used to make these cups, prophy or polishing pastes can be impregnated into the cups, thus eliminating the need to dispense and apply a separate paste.

The foam cups can be selected with a different range of softness, thus permitting use on dentin and enamel. Furthermore, desensitizing agents can be applied using this method. Even dentin bonding could be more completely impregnated into the dentin and the dentin smear layer using this method.

Conventional methods of contouring, finishing and polishing employ the use of flexible discs with grades ranging from course, medium, fine and extra-fine. These discs, when used in sequence, do not produce a highly reflective polished surface on small particle glass or hybrid composite materials. Nevertheless, the pressure sensitive polishing disc can be fabricated with an indentation in the center of the adhesive side to allow placement directly on one of these conventional, commercially available discs. The surface can then be polished with this polishing element and appropriate polishing paste. This approach eliminates the need for a separate rubber cup for polishing and produces a surface superior to rubber cup and paste polishing. Nevertheless, the use of conventional multiple discs is time-consuming and the method of Example 1 eliminates many of these multiple disc steps.

While present embodiments of the invention and methods of practicing the same have been illustrated and described, it will be recognized by those skilled in the art that this invention may be otherwise variously embodied and practiced within the scope of the following claims.

What is claimed is:

1. An abrasive implement for gross reduction and shaping of composites which simultaneously reduces filler and resin in the composite comprising:
   a. about 19-35% elastomeric polymer,
   b. about 1-5% pyrogenic silica, and
   c. about 60-80% abrasive powder having a hardness greater than the hardness of said composite filler.

2. The abrasive implement according to claim 1 in which the elastomeric polymer is formed from the polymerization of an alkyl urethane prepolymer having a molecular weight between about 1500 and 2500 and having a viscosity of about 10,000–35,000 cps at 25° C. and in which the abrasive powder has a hardness of between about 5.5–10 on the mohs scale of hardness.

3. The abrasive implement according to claim 1 in which the abrasive powder is aluminum oxide.

4. The abrasive implement according to claim 1 in which the elastomeric polymer is formed from a light cured prepolymer.

5. The abrasive implement according to claim 1 in which the elastomeric polymer is formed from a thermally cured prepolymer.

6. The abrasive implement according to claim 1 in which the elastomeric polymer is formed from a chemically cured prepolymer.

7. The abrasive implement according to claim 1 in which said abrasive powder comprises about 70% by weight of said implement.

8. The abrasive implement according to claim 1 in which said prepolymer comprises the reaction product of polyalkylene glycol, alkylene diisocyanate and a hydroxyalkyl ester of an ethylenically unsaturated carboxylic acid.

9. The abrasive implement according to claim 2 in which said prepolymer comprises the reaction product of polyalkylene glycol, alkylene diisocyanate and a hydroxyalky ester of an ethylenically unsaturated carboxylic acid.

* * * * *